United States Patent [19]

Hilscher et al.

[11] Patent Number: 5,049,508
[45] Date of Patent: Sep. 17, 1991

[54] APPARATUS AND PROCESS FOR TOTAL SULFUR DETERMINATION

[75] Inventors: Willi Hilscher, Wesel; Cetin Gokcek, Mulheim/Ruhr; Dietrich Schmicker, Neukirchen-Vluyn; Eberhard Riedel, Moers; Peter Kunik, Ratingen, all of Fed. Rep. of Germany

[73] Assignee: Messer Griesheim GmbH, Fed. Rep. of Germany

[21] Appl. No.: 260,872

[22] Filed: Oct. 21, 1988

[30] Foreign Application Priority Data

Oct. 21, 1987 [DE] Fed. Rep. of Germany ....... 3735599

[51] Int. Cl.⁵ .......................................... G01N 33/00
[52] U.S. Cl. .................................... 436/123; 436/119; 436/121; 436/161; 422/89; 422/78; 422/83; 73/23.35; 73/23.41; 55/356
[58] Field of Search ................ 436/119, 121, 123, 161; 422/89, 78, 80, 83; 73/23.35, 23.41; 55/67, 73, 356

[56] References Cited

U.S. PATENT DOCUMENTS

| | | | |
|---|---|---|---|
| 3,264,124 | 8/1986 | Lauder et al. | 106/65 |
| 4,012,337 | 3/1977 | Mitchell | 252/439 |
| 4,371,458 | 2/1983 | Eastman et al. | 252/439 |
| 4,687,749 | 8/1987 | Beall | 501/5 |
| 4,767,791 | 8/1988 | Nakajima et al. | 518/712 |

FOREIGN PATENT DOCUMENTS 55-110953A 8/1980 Japan .

OTHER PUBLICATIONS

CA 106(18): 140800t, Hilscher, W. et al., "For Environmental Protection: A Superior Method for Sulfur Determination in Petroleum Products", Gas Aktuell 1986, 32. 31-4.
Willard, H. H. et al., "Instrumental Methods of Analysis", New York, D. Van Nostrand Co., 1981, p. 455.

Primary Examiner—David L. Lacey
Assistant Examiner—David Redding
Attorney, Agent, or Firm—Connolly & Hutz

[57] ABSTRACT

The total sulfur content of samples consisting of chemical compounds is determined by the use of gas chromatographic separation of the sulfur and its flame-photometric detection. The samples are subjected to a catalytic reaction in a pipe reactor before the separation whereby all sulfur-containing compounds are completely converted into hydrogen sulfide. The pipe reactor is made from an aluminum oxide material in a purity of at least 99.8% of the corundum type.

16 Claims, 3 Drawing Sheets

APPARATUS AND PROCESS FOR TOTAL SULFUR DETERMINATION

BACKGROUND OF THE INVENTION

A major objective in environmental protection is to minimize the emission of harmful substances. Sulfur dioxide ($SO_2$) produced in combustion processes of mineral oil products such as heating oil, gasoline, diesel fuel, heating gas has a substantial fraction of harmful substance emission. To limit these emissions, fuels having the lowest possible sulfur content must be employed. For this purpose, these fuels must be constantly examined according to a quick and sensitive analysis process for their total sulfur content.

The combustion according to Wickbold is used as standard analysis process. This analysis method is described in DIN-EN 41. This method requires considerable chemical-apparative expense. The duration of several hours for a single analysis is a great disadvantage, in particular, rechecking the analysis is expensive and technically not interesting since the process parameters may have changed in the long interim time following the analysis-taking. Monitoring and controlling the reaction processes in petro-chemical plants by determining the total sulfur content is, therefore, not possible.

SUMMARY OF THE INVENTION

The invention is based on the objective of providing an analysis method in which the total sulfur content can be quickly and accurately determined.

With the analysis method according to the invention, an analysis can be conducted in about two minutes. As a result, a quick analysis sequence and, therefore, a higher sample throughput is obtained.

The invention requires only small amounts of samples in the order of magnitude of 1 ul for liquid samples. Metering may take place manually or by means of an automatic sample charging system which additionally improves the reproducibility.

The analysis method according to the invention is well suited for routine operations because of its extensive automation and can also be conducted by trained operating personnel.

Another advantage is the lower detection limit of 0.3 mg S/kg sample. This represents a considerable improvement over DIN-EN 41 which specifies a lower detection limit of at least 1 mg S/kg sample.

The invention operates according to the principle of reaction gaschromatography. The specific detection takes place by a sulfur-sensitive flame-photometer detector. The combination of catalytic reaction and gaschromatographic separation provides for the undisturbed detection (no cross sensitivity) with the flame-photometer detector.

After complete evaporation, the sample is fed into a pipe reactor in which all sulfur-containing compounds of the sample are catalytically hydrated to $H_2S$. In this process, the hydrocarbons of the sample are also hydrated while low molecular components are formed. The produced hydrogen sulfide is then separated gaschromatographically and determined flame-photometrically.

THE DRAWINGS

An exemplified embodiment is shown in the drawings and described in more detail.

DETAILED DESCRIPTION

Figure 1:
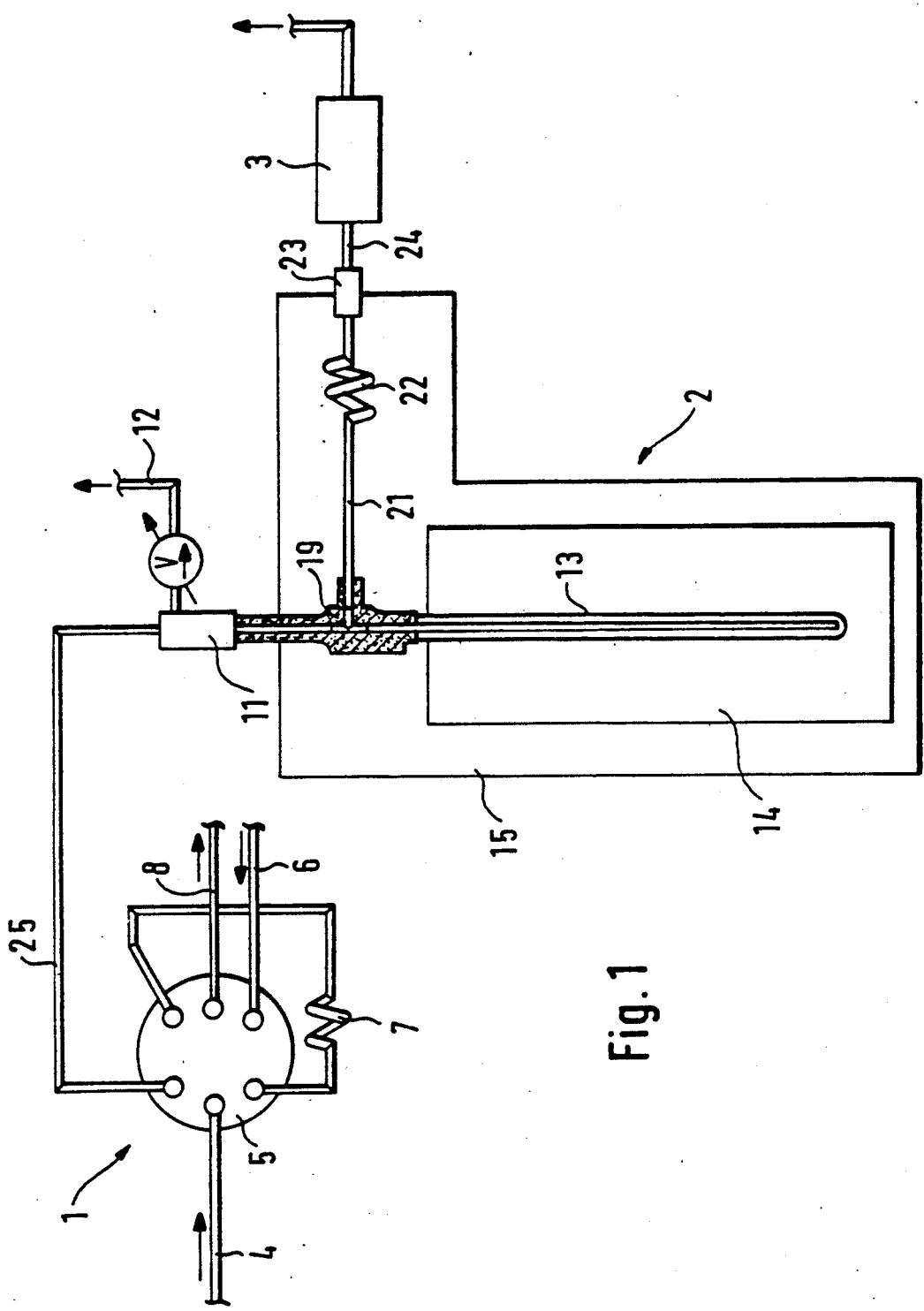
FIG. 1 shows the setup of the analysis equipment for gases.

The analysis equipment consists of the three main groups: charge system 1, gaschromatograph 2 with pipe reactor 13 and flame-photometer detector 3.

The gas metering valve 5 receives the gaseous sample mixture via a heated PTFA line 6. The chemical compounds to be employed may have an organic or inorganic nature in the combinations of sulfur with the elements of the fourth, fifth, sixth or seventh main group of the periodic system of the elements. The samples may be introduced into the analysis equipment in the form of pure substances or dissolved in solvents. The invention is particularly suitable for mixtures from the field of mineral oils and mineral oil products.

Hydrogen is used as the carrier gas for the sample mixture. Feeding takes place via the line 4. The unused sample mixture is discharged via line 8; 7 designates a gas metering loop. The gas metering valve 5 is turned by hand or, preferably, by means of a stepping motor.

Figure 2:
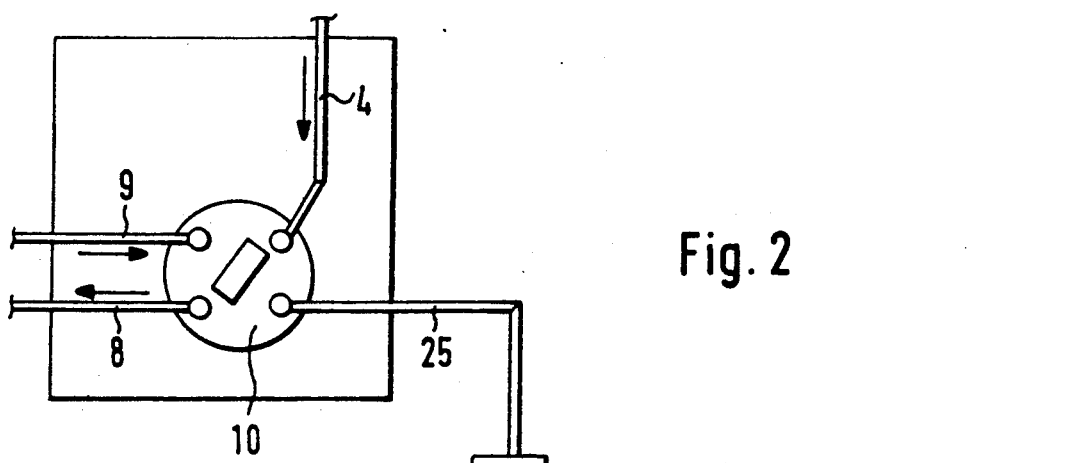
FIG. 2 shows the same equipment with a charge system for gases liquified under pressure
Figure 3:
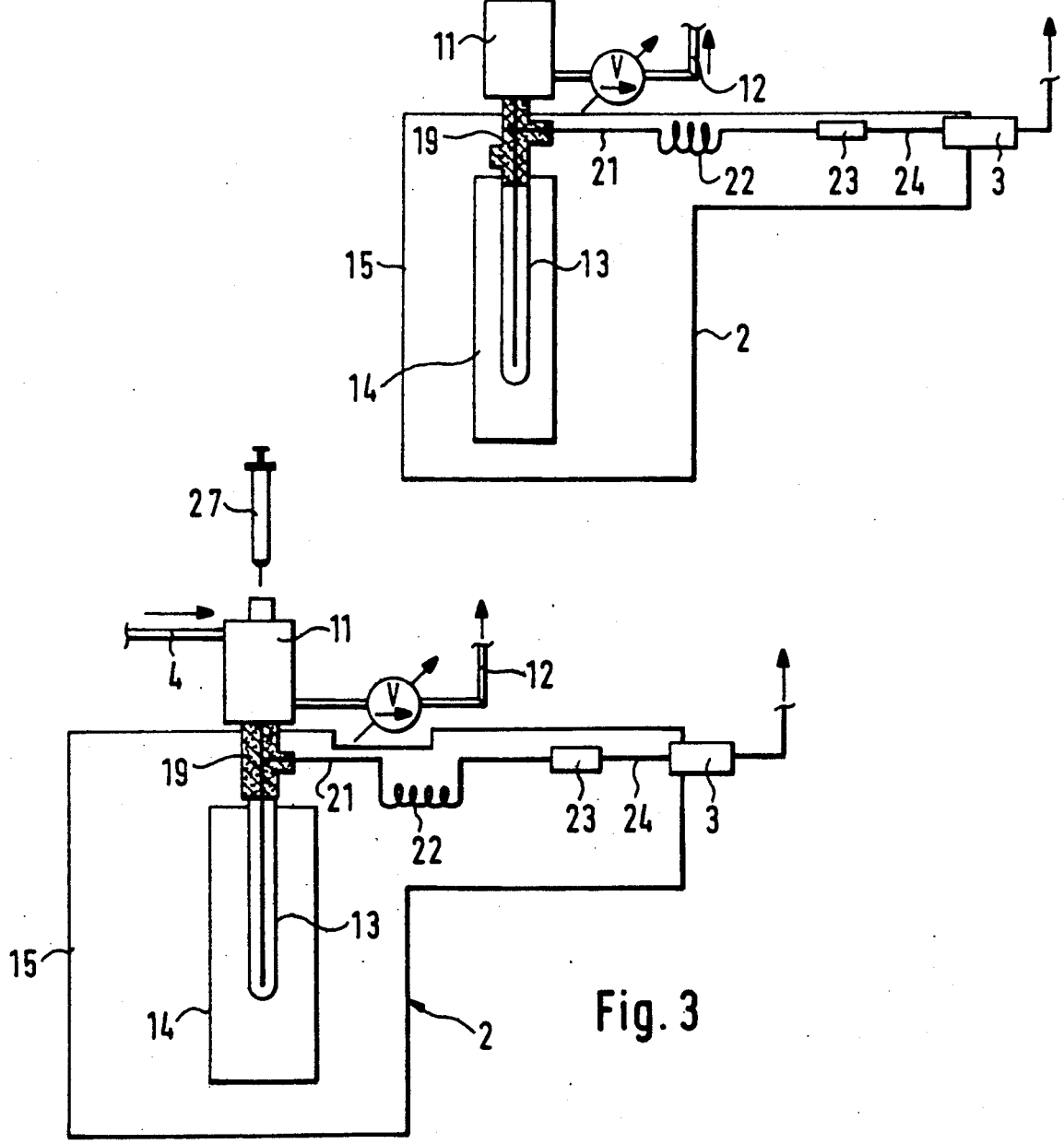
FIG. 3 shows this analysis equipment with a charge system for liquids.

Samples of gases liquified under pressure are introduced in the charging device 10 under precooling. Precooling prevents a premature evaporation of substances which under normal conditions are present in the two-phase area during withdrawal; 4 again designates the feed for the carrier gas, 9 the sample feed line and 8 the line for discharging the unused sample mixture (FIG. 2).

The liquids are metered with a metering syringe 27 by hand or automatically directly into the injector 11 in which the liquid sample is evaporated completely and suddenly. The excess sample gas is discharged via the line 12. The carrier gas is fed to the injector via the line 4. The gaseous sample is admitted to the pipe reactor 13 via the shortest path.

The gaseous samples are fed to the injector 11 via a capillary 25. The capillary consists of commercially coated quartz material. To avoid a dead volume, the capillary 25 extends into the injector 11 as well as into the gas metering valve 5. The pipe reactor 13 is connected to the injector 11 via a T-section 19. The T-section 19 consists of ceramic material, preferably, silicon dioxide, aluminum oxide and magnesium oxide. A preferred composition is 46% $SiO_2$, 16% $Al_2O_3$ and 17% $MgO$.

Figure 4:
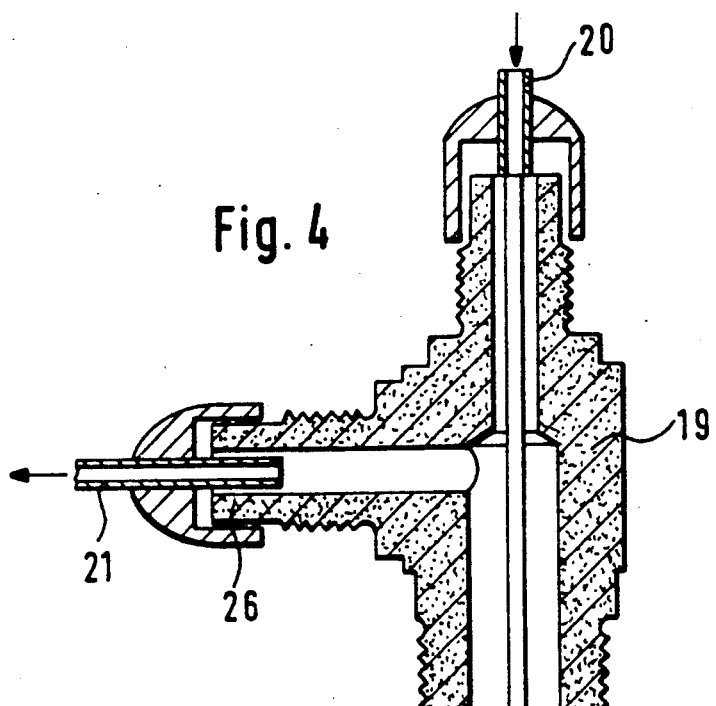
FIG. 4 shows the pipe reactor in cross section.
Figure 4:
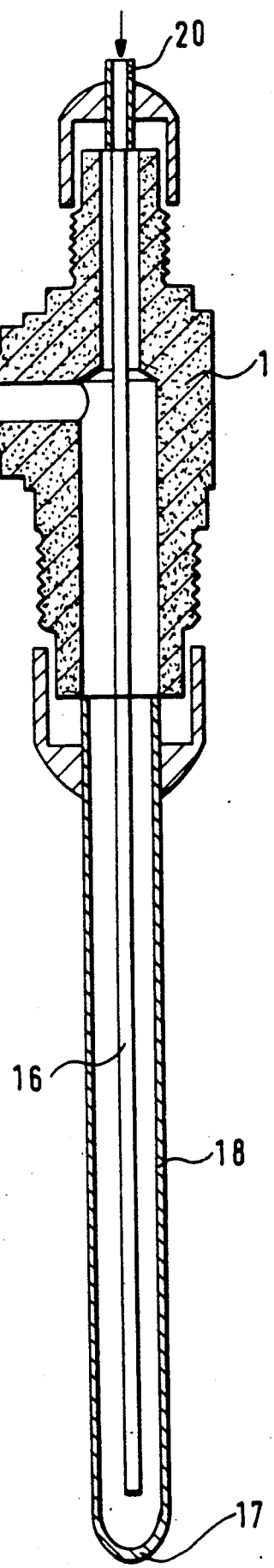
Figure 5:
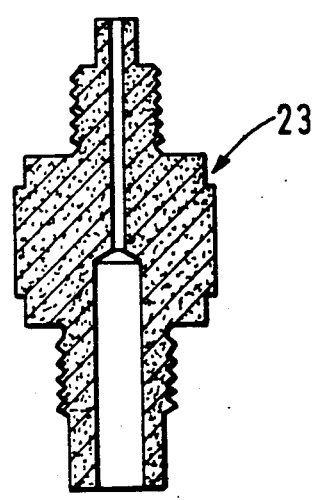
FIG. 5 shows the coupling section between separation column and detector.

The pipe reactor (FIG. 4) is placed in a heating device 14 which keeps the reaction space at a temperature ranging from 500° C. to 1400° C. with a deviation of about ±2° C. The preferred reaction temperature lies in the upper range, preferably, at 1150° C. The heating device is arranged in the main oven 15 of the gas chromatograph and, preferably, consists of fire brick and a platinum wire heating system which are surrounded by a metal jacket.

The pipe reactor 13 consists of two concentrically arranged pipes 16 and 18 whereby the inside pipe 16 reaches close to the end of the pipe 18. In order to achieve a smooth flow and uniform reversal without changing the pressure relationships, the pipe 18 is provided on this end with a semi-spherical closure 17. The two pipes 16, 18 are fastened in a T-section 19. The pipes 16 and 18 according to the invention consist of aluminum oxide of the corundum type ($\alpha$-Al$_2$O$_3$) in a purity of 99.8%.

In a preferred exemplified embodiment of the reactor 13 with concentric pipes 16, 18 the distance between the outside wall of the pipe 16 and the inside wall of the pipe 18 is 0.5 to 4 mm, preferably, 0.8 to 1.5 mm.

The gaseous sample arrives through the inlet 20 into the pipe reactor 13, flows first through the inside pipe 16 and is then reversed into the outside pipe 18. In this pipe 18, the sample flows upward into the T-section 19 and leaves this section through the separation column connection 21 at the reactor outlet. During travel through the pipe reactor 13, the catalytic reaction takes place whereby, in particular, as a result of the large reaction area and the material according to the invention, all sulfur-containing compounds are completely converted into hydrogen sulfide.

The separation column 22 is connected to the separation column connection 21 at the reactor outlet. This is a packed column which separates the products from the catalytic hydration. The separation column 22 is kept at a temperature of 80° C.

At the outlet of the separation column 22, a coupling section 23 is provided from where a capillary 24 leads to the flame-photometer detector 3. The coupling section 23 preferably is made of the same material as the T-section 19.

The analysis equipment according to the invention is calibrated by gravimetrically produced, calibrated samples. In the exemplified embodiment, dimethyl sulfide in benzol is used for the calibration.

The peak area of the hydrogen sulfide is plotted over the amount of sulfur in the calibration curve. Accordingly, the total sulfur content can be indicated when the density of the sample is known.

Samples with up to 1000 mg S/kg can still be directly metered. Higher contents definitely require dilution.

In a preferred process for the operation of the analysis equipment according to the invention, the flow of the gas in the reactor 13 at an inlet pressure of about 1.8 bar is 25-60 ml/min. preferably, 40-50 ml/min. The effective average dwell time in the reactor is then 1.5-3.5 sec. preferably, 2 to 3 sec. The temperature in the reactor space is 500° to 1400° C., preferably, 1150° C. with a temperature tolerance of ±2° C.

We claim:

1. In an apparatus for the determination of the total sulfur content of samples consisting of chemical compounds having means for gas chromatographic separation of the sulfur and its flame-photometric detection, the apparatus including a charge system in flow communication with a gas chromatograph section which in turn is in flow communication with a detector section, the sample being fed from the charge system into a pipe reactor in the gas chromatograph section for catalytic reaction in the pipe reactor before the separation of the sulfur, the improvement being in that said pipe reactor is made of aluminum oxide in a purity of at least 99.8% of the corundum type (L-Al$_2$O$_3$) whereby said pipe reactor catalytically converts all sulfur-containing compounds in the sample into hydrogen sulfide.

2. Apparatus according to claim 1, wherein said pipe reactor is a single pipe.

3. Apparatus according to claim 1, wherein said pipe reactor comprises a pair of concentric pipes.

4. Apparatus according to claim 1, further including a T-section connected to said pipe reactor, said T-section having an inlet communicating with said charge system and having an outlet communicating with said detector section, and said T-section being made of a silicon dioxide, aluminum oxide and magnesium oxide-based glass ceramic material.

5. Apparatus according to claim 4, wherein said charging system includes a gas metering valve, a capillary extending from said gas metering valve and communicating with said pipe reactor.

6. Apparatus according to claim 5, wherein said capillary communicates with said pipe reactor through an injector.

7. Apparatus according to claim 5, wherein said gas metering valve has an inlet containing a temperature measuring instrument and has an outlet containing a pressure measuring instrument.

8. Apparatus according to claim 3, wherein said concentric pipes are positioned and arranged so that the distance between the outside wall of the interior pipe and the inside wall of the exterior pipe is 0.5-4 mm.

9. Apparatus according to claim 8, wherein said concentric pipes are positioned and arranged so that the distance between the outside wall of the interior pipe and the inside wall of the exterior pipe is 0.8-1.5 mm.

10. Apparatus according to claim 1, wherein said pipe reactor is mounted in a thermally insulated furnace, and said reactor having a reaction space at a temperature of 500°-1400° C.

11. In a process for determining the total sulfur content of samples taken from a larger quantity of sulfur containing material including feeding the sample from a charge system to a pipe reactor in a gas chromatograph section, catalytically reacting the sample in the pipe reactor in the gas chromatograph section before a separation step, the improvement being in that using as the pipe reactor a pipe reactor made from aluminum oxide in a purity of at least 99.8% of the corundum type, and flowing gas in the pipe reactor at a flow rate of 25-60 ml/min. at an inlet pressure of about 1.8 bar so that said pipe reactor catalytically converts all sulfur containing compounds into hydrogen sulfide.

12. Process according to claim 11, wherein the gas flow rate is 40-50 ml/min.

13. Process according to claim 11, including maintaining the gas in the reactor for an average dwell time of 1.5-3.5 seconds.

14. Process according to claim 13, wherein the average dwell time is 2-3 seconds.

15. Process according to claim 11, wherein the reactor has a reaction space, and maintaining the temperature in the reaction space at 500°-1400° C. at a temperature tolerance of ±2° C.

16. Process according to claim 11, wherein the temperature is about 1150° C.

* * * * *